US005792618A

United States Patent [19]

Starkweather et al.

[11] Patent Number: 5,792,618
[45] Date of Patent: Aug. 11, 1998

[54] LIQUID SINGLE-COMPONENT SUBSTRATES FOR DETECTION OR ASSAY OF HORSERADISH PEROXIDASE

[75] Inventors: William H. Starkweather, Gaithersburg; Ronald Telford, Pasadena, both of Md.

[73] Assignee: Moss, Inc., Hanover, Md.

[21] Appl. No.: 720,383

[22] Filed: Sep. 27, 1996

[51] Int. Cl.[6] .................................................. C12Q 1/28
[52] U.S. Cl. .............................. 435/28; 435/25; 435/805
[58] Field of Search ................................ 435/7.1, 7.92, 435/7.94, 25, 28, 805; 436/531

[56] References Cited

U.S. PATENT DOCUMENTS 4,503,143  3/1985  Gerber et al. ............................ 435/7
5,013,646  5/1991  Woiszwillo ............................ 435/7.92
5,641,639  6/1997  Perry .................................... 435/7.92

FOREIGN PATENT DOCUMENTS 7-111899  5/1995  Japan .
8-89291   4/1996  Japan .
WO 86/05207  9/1986  WIPO .

Primary Examiner—Ralph Gitomer
Attorney, Agent, or Firm—Robert R. Meads

[57] ABSTRACT

Colorless single component TMB reagents for the detection of HRP and their processes of manufacture including the encapsulation of substrate within a cyclodextrin cavity are described.

22 Claims, No Drawings

LIQUID SINGLE-COMPONENT SUBSTRATES FOR DETECTION OR ASSAY OF HORSERADISH PEROXIDASE

BACKGROUND OF INVENTION

The present invention relates to substrates for detecting specific analytes in the field of immunology and molecular biology and, more particularly, to improvements in liquid single-component substrates for detection or assay of horseradish peroxidase (HRP) and their methods of manufacture.

HRP is an enzyme commonly employed for detecting specific analytes in the fields of immunology and molecular biology. Some, but not all of methods employed in these fields include enzyme linked immunoabsorbant assays (ELISA), Western, Northern and Southern blot procedures and in situ hybridization techniques. Substrates to detect HRP should be sensitive and preferably supplied as a single component solution containing all necessary active ingredients. Further, such products should display extended shelf life preferably at room temperature and should not degrade in laboratory incandescent and fluorescent light.

Commercial sources for HRP substrates exist e.g. Sigma Chemical Co., Kirkegarrd and Perry Laboratories, Inc., Elisa Technologies, Inc. and Transgenic Sciences, Inc. However, such substrates are not characterized by extended shelf life at room temperature or stability in the presence of laboratory incandescent or fluorescent light.

Accordingly, there is a need for improved substrates for detection of HRP which are characterized by extended shelf life and stability in the presence of laboratory light. The present invention provides such substrates and methods for manufacturing such substrates.

SUMMARY OF INVENTION

The present invention relates to the production of single solution substrates for detection and or quantitation of HRP labeled probes used in the fields of immunology and molecular biology. The production process is unique in that numerous timed steps are involved relating to pH and pK of the substrate being solubilized and stabilized. The timed steps are necessary for formation of specific substrate salts soluble in a final buffer formulation. The timed steps are also necessary for encapsulation of the substrate within a cyclodextrin cavity which characterizes the substrates of the present invention.

More particularly, the present invention provides a unique manufacturing process that allows production in bulk quantities of single solution substrates for HRP [3, 3', 5, 5' tetramethylbenzidine (TMB)] used in ELISA procedures and a precipitating TMB utilized for blotting techniques.

Further, in the process of the present invention the addition of polyhydroxy alcohols such as 1, 2, 6-hexanetriol prevents the formation of oxidizing species such as $OH$, $O_2^-$ and $H_2O_2$.

Still further, the addition of ethylenediamine tetracetic acid at a specific pH also provides protection from oxidation and chelates transition metal salts such as iron and copper preventing further radical formation via Fenton-Haber-Weiss reactions; an indication of such a reaction being the presence of a blue color (TMB).

Specifically, the use of cyclodextrins, such as hydroxypropyl-beta-cyclodextrin, with a precise degree of substitution, imparts excellent stability to substrates for HRP produced by the process of the present invention. In particular, the methods of addition of such cyclodextrins are critical to the process as are the incorporation of polyhydroxy alcohols and the times of incubation and the adjustment of pH.

A particularly important characteristic of the reagents produced by the process of the present invention is that they provide zero order kinetics over the routine period required for assay. This is to be contrasted to other products providing a higher initial signal, which exhibit first order or even second order rate reactions. Specifically the products of the present invention obey zero order kinetics and thus give real numbers with respect to analyte levels.

Thus, in summary, the present invention involves encapsulation of active product by cyclodextrin derivatives and incorporation of radical trapping compounds that prevent auto-oxidation of the preferred substrate. Further, the process of the present invention provides colorless single component reagents exhibiting excellent stability at room temperature and displaying kinetic properties that allow accurate quantitation (ELISA) and detection (Blotting procedures) of analytes useful in the diagnosis of diseases in man, animal and plant domains.

DETAILED DESCRIPTION OF THE INVENTION

In the following description, HCl shall mean 6 mol/L hydrochloric acid; DMSO shall mean ACS dimethylsulfoxide; TMB shall mean 3,3',5,5'-tetramethylbenzidine, free base, anhydrous; HPBCD shall mean hydroxypropyl-beta-cyclodextrin; THH shall mean 1, 2, 6-trihydroxyhexane; NaAc shall mean ACS sodium acetate, anhydrous; EDTA shall mean ethylenediamine tetracetic acid; HOOH shall mean hydrogen peroxide; IPA shall mean isopropyl alcohol; DI shall mean validated deionized water; and NP-+b 4 shall mean Niaproof-4 a surfactant, comprising sodium 7-ethyl-2-methyl-4-undecyl sulfate, produced by Union Carbide and Being a trademark of Niacet Corporation.

As previously noted, TMB has rapidly gained acceptance as an excellent peroxidase substrate for use in HRP based ELISA and Western, Northern and Southern blotting techniques. The reaction mechanisms of such techniques are well known and include chemical changes that occur following one and two electron oxidations by HRP in the presence of hydrogen peroxide. The charge-transfer complex of such a reaction shows absorption maxima at 370 and 653 nm and is a 1-electron oxidation product. It is in rapid equilibrium with a cation free radical. Further oxidation leads to the formation of a diimine absorbing at 450 nm. Such a charge transfer complex also may be formed in the absence of peroxides. In either event, the formation of the charge transfer complex should be prevented if a colorless reagent is to be produced.

The sequence of additions in the manufacturing process described below prevents non-enzyme oxidation and eliminates precipitation of TMB during the production procedure. These described techniques render the final product insensitive to normal laboratory lighting conditions and result in a commodity that may be stored for at least 18 months at room temperature.

In the practice of such techniques the HPBCD concentrations necessary for complete solubilization of the TMB range in final solution concentrations from 4 mMol/L to 10 mMol/L with the preferred concentration being 6 mMol/L. Also, the HPBCD solution should be prepared at least 4 hours prior to use with the preferred time being a minimum of 20 hours. Further, in the following procedures, Mannitol can replace THH in the system and acts in a similar fashion protecting TMB from oxidation by $O_2-$ and OH. In a similar fashion, 1,4-cyclohexanediol also affords protection. Still further, THH should be prepared a day prior to production, similar to HPBCD, and final concentrations of THH in the product may range from 0.042 Mol/L to 0.6 Mol/L with 0.414 Mol/L being the preferred concentration.

The following examples set forth detailed production procedures for TMB solutions applicable to ELISA and membrane methods for batch sizes of 200 liters.

EXAMPLE 1

PRODUCTION OF A TMB SOLUTION FOR ELISA METHODS

The reagents to form the TMB ELISA solution, the reagent concentrations per liter, the reagent concentrations per batch, the preferred final mole per liter concentration of each reagent and the permissible range of the final mole per liter concentration for each reagent are set forth in the following table.

| REAGENT | REQD/L | REAGENTS REQD/BATCH | FINAL | RANGE |
|---------|--------|---------------------|---------|----------------|
| HCl     | 4.32 mL | 864 mL             | 0.026   | 0.02–0.035     |
| DMSO    | 10.0 mL | 200 mL             | 0.128   | 0.10–0.25      |
| TMB     | 0.3 g   | 60 g               | 0.00125 | 0.001–0.003    |
| HPBCD   | 9.0 g   | 1800 g             | 0.006   | 0.004–0.01     |
| THH     | 55.5 g  | 11000 g            | 0.414   | 0.042–0.6      |
| NaAc    | 8.2 g   | 1640 g             | 0.10    | 0.07–0.16      |
| EDTA    | 0.24 g  | 48 g               | 0.0006  | 0.0004–0.004   |
| IPA     | 2.5 mL  | 500 mL             | 0.0325  | 0.025–0.060    |
| HOOH    | 2.5 mL  | 500 mL             | 0.0022  | 0.0011–0.0033  |

PROCEDURES TO BE COMPLETED THE DAY PRIOR TO PRODUCTION

Deionized Water Validation

1. Measure the resistance of the deionized water and record the measured value.
2. Measure the parts/million of dissolved solids in the deionized water and record the measured value.
3. The resistance should be greater than 18 megohms with no more than 0.05 ppm total solids. If not, change the resin bed for filtering the water and recheck the water as set forth above.

Preparation of Sodium Acetate (NaAc) Solution

1. Dissolve the required amount of NaAc in 8.7 L of validated DI water.
2. Store in a refrigerator until needed.

Preparation of HPBCD Solution

1. To an appropriate sized container, add approximately 3 L of validated DI water.
2. Add the calculated amount of HPBCD to the container.
3. Fill a batch tank with 8.7 L of validated DI water and let the batch stand for 2 hours.
4. Add the mixture of HPBCD and DI water from the container to the batch tank and stir until the mixture is dissolved. Then let the solution stand at room temperature until needed.

Preparation of THH Solution

1. Add the calculated amount of THH to an appropriate sized container.
2. Add 7.4 L of validated DI water to the container.
3. Mix thoroughly and let the solution stand at room temperature until needed.

PRODUCTION PROCEDURE

1. Add the calculated amount of HCl to a batch tank filled with water the day before.
2. With a conventional mixer, mix the contents of the tank.
3. Measure the required volume of DMSO into an appropriate container and add the calculated quantity of TMB.
4. Stir the mixture of DMSO and TMB until dissolved.
5. Add the mixture to the batch tank and stir for 15 minutes.
6. Add to the batch tank the HPBCD solution prepared the previous day and stir for 35 minutes.
7. Add to the batch tank the THH solution prepared the previous day and stir for 45 minutes.
8. Adjust the pH of the solution in the batch tank to 2.68 with the NaAc solution prepared the previous day, adding at a flow rate of 45–90 mL/minute.
9. When a pH of 2.68 is reached, stop the addition of the NaAc solution and let the batch stir for 45 min.
10. After 45 minutes, adjust the pH to 3.8 with the NaAc solution, adding at the same flow rate.
11. Let the batch stand covered for at least 64 hours.
12. After 64 hours and with a spectrophotometer, scan the resulting solution between 900–300 nm and note the shape of the resulting spectrum.
13. Adjust the pH of the batch to 4.28 with the NaAc solution. Rescan between 900–300 nm and note the shape of the spectrum.
14. Dissolve the calculated amount of EDTA in 400 mL of validated DI water.
15. Add the EDTA solution to the batch and stir for 5 minutes. Note any pH change in the solution. It should not exceed 0.2 pH units.
16. Adjust the pH of the batch to 4.9 with the NaAc solution. Rescan between 900–300 nm and note the shape of the spectrum.
17. Continue to stir until no inflections are noted at 650 nm, 450 nm and 370 nm.
18. After the spectrum shows no inflections at 650 nm, 450 nm and 370 nm, add the calculated volume of HOOH to the batch.
19. Add the calculated volume of IPA to the batch.
20. Add DI to adjust the volume of the batch to 200 liters.
21. Stir for at least 1 hour, then bottle in appropriate containers.

EXAMPLE 2

PRODUCTION OF A TMB SOLUTION FOR MEMBRANE ASSAYS

The reagents to form the TMB membrane solution, the reagent concentrations per liter, the reagent concentrations per batch, except for NP-4, the preferred final mole per liter concentration of each reagent and the permissible range of the final mole per liter concentration for each reagent are set forth in the following table. The final concentration and range of concentration for NP-4 are expressed as the percent volume of NP-4 per liter of solution.

| REAGENTS | | | | |
|---|---|---|---|---|
| REAGENT | REQD/L | REQD/BATCH | FINAL | RANGE |
| HCl | 4.32 mL | 864 mL | 0.026 | 0.02–0.035 |
| DMSO | 10.0 mL | 200 mL | 0.128 | 0.10–0.25 |
| TMB | 0.3 g | 60 g | 0.00125 | 0.001–0.003 |
| HPBCD | 9.0 g | 1800 g | 0.006 | 0.004–0.01 |
| THH | 55.5 g | 11000 g | 0.414 | 0.042–0.6 |
| NaAc | 8.2 g | 1640 g | 0.10 | 0.07–0.16 |
| EDTA | 0.24 g | 48 g | 0.0006 | 0.0004–0.004 |
| IPA | 2.5 mL | 500 mL | 0.0325 | 0.025–0.060 |
| HOOH | 2.5 mL | 500 mL | 0.0022 | 0.0011–0.0033 |
| NP-4 | 1.07 mL | 214 mL | 0.107% | 0.10–0.20% |

PROCEDURES TO BE COMPLETED THE DAY PRIOR TO PRODUCTION

Deionized Water Validation

1. Measure the resistance of the deionized water and record the measured value.
2. Measure the parts/million of dissolved solids in the deionized water and record the measured value.
3. The resistance should be greater than 18 megohms with no more than 0.05 ppm total solids. If not, change the resin bed for filtering the water and recheck the water as set forth above.

Preparation of Sodium Acetate (NaAc) Solution

1. Dissolve the required amount of NaAc in 8.7 L of validated DI water.
2. Store in a refrigerator until needed.

Preparation of HPBCD Solution

1. To an appropriate sized container, add approximately 3L of validated DI water.
2. Add the calculated amount of HPBCD to the container.
3. Fill a batch tank with 8.7 L with validated DI water and let stand for 2 hours.
4. Add the mixture of HPBCD and DI water from the container to the batch tank and stir until the mixture is dissolved. Then let the solution stand at room temperature until needed.

Preparation of THH Solution

1. Add the calculated amount of THH to an appropriate sized container.
2. Add 7.4. L of validated DI water to the container.
3. Mix thoroughly and let the mixture stand at room temperature until needed.

PREPARATION OF NP-4 SOLUTION

1. To 15 L of DI water in an appropriate size container, add 180 g of HPBCD and stir until dissolved.
2. Add 1100 g of THH and mix well.
3. Add 86 mL of HCl and mix well.
4. Adjust the pH of the mixture of step 3 to 4.28 with the NaAc solution.
5. Add 4.8 g of EDTA to the solution and stir until dissolved.
6. Adjust the pH of the solution to 4.90 with the NaAc solution.
7. Add sufficient DI water to adjust the volume of the solution to 20 L and let the solution stand at least 64 hours.

PRODUCTION PROCEDURE

1. Add the calculated amount of HCl to a batch tank filled with water the day before.
2. Mix the contents of the tank.
3. Measure the required volume of DMSO into an appropriate container and add the calculated quantity of TMB.
4. Stir the mixture of DMSO and TMB until dissolved.
5. Add the mixture to the batch tank and stir for 15 minutes.
6. Add to the batch tank the HPBCD solution prepared the previous day and stir for 35 minutes.
7. Add to the batch tank the THH solution prepared the previous day and stir for 45 minutes.
8. Adjust the pH of the solution in the batch tank to 2.68 with the NaAc solution prepared the previous day, adding at a flow rate of 45–90 mL/minute.
9. When a pH of 2.68 is reached, stop the addition of the NaAc solution and let the batch stir for 45 min.
10. After 45 minutes, adjust the pH to 3.8 with the NaAc solution, adding at the same flow rate.
11. Let the batch stand covered for at least 64 hours.
12. After 64 hours and with a spectrophotometer, scan the resulting solution between 900–300 nm and note the shape of the resulting spectrum.
13. Adjust the pH of the batch to 4.28 with the NaAc solution. Rescan between 900–300 nm and note the shape of the spectrum.
14. Dissolve the calculated amount of EDTA in 400 mL of validated DI water.
15. Add the EDTA solution to the batch and stir for 5 minutes. Note any pH change in the solution. The change should not exceed 0.2 pH units.
16. Adjust the pH of the batch to 4.9 with the NaAc solution. Rescan between 900–300 nm and note the shape of the spectrum.
17. Continue to stir until no inflections are noted at 650 nm, 450 nm and 370 nm.
18. After the spectrum shows no inflections at 650 nm, 450 nm and 370 nm, add the calculated volume of HOOH to the batch.
19. Add the calculated volume of IPA to the batch.
20. Add DI water to adjust the volume of the batch to 180 liters.
21. Add the NP-4 solution to the batch at a flow rate of 200 mL/minute.
22. After the addition of NP-4 is complete, continue stirring for at least 60 hours.
23. After 60 hours of stirring, bottle the resulting TMB solution in appropriate containers.

While specific examples of the manufacturing procedures of the present invention have been presented above, the concentration ranges of the reagents set forth in the foregoing tables indicate that the specific examples are presented by way of illustration only. Changes within the concentration ranges may be made without departing from the present invention, the scope of which is to be limited only by the following claims.

We claim:

1. A colorless 3,3',5,5'-tetramethylbenzidine (TMB) reagent for detection or assay of horseradish peroxidase (HRP), comprising a solution of:

hydrochloric acid (HCl) in a concentration of 0.02 to 0.35 moles per liter;

dimethylsulfoxide (DMSO) in a concentration of 0.10 to 0.25 moles per liter;

TMB in a concentration range of 0.001 to 0.003 moles per liter;

hydroxypropyl-beta-cyclodextrin (HPBCD) in a concentration range of 0.004 to 0.01 moles per liter;

1,2,6-hexanetriol (THH) in a concentration range of 0.042 to 0.6 moles per liter;

sodium acetate (NaAc) in a concentration range of 0.07 to 0.16 moles per liter;

ethylenediamine tetraacetic acid (EDTA) in a concentration range of 0.0004 to 0.004 moles per liter;

isopropyl alcohol (IPA) in a concentration range of 0.025 to 0.060 moles per liter; and hydrogen peroxide (HOOH) in a concentration range of 0.0011 to 0.0033 moles per liter.

2. The reagent of claim 1 further comprising:

sodium 7-ethyl-2-methyl-4-undecyl sulfate (NP-4) in a volume percent concentration of 0.1 to 0.2%.

3. The reagent of claim 2 wherein the concentration of NP-4 is 0.107% by volume.

4. The reagent of claim 1 wherein the concentration of HCl is 0.026 moles per liter.

5. The reagent of claim 1 wherein the concentration of the DMSO is 0.128 moles per liter.

6. The reagent of claim 1 wherein the concentration of TMB is 0.00125 moles per liter.

7. The reagent of claim 1 wherein the concentration of HPBCD is 0.006 moles per liter.

8. The reagent of claim 1 wherein the concentration of THH is 0.414 moles per liter.

9. The reagent of claim 1 wherein concentration of NaAc is 0.10 moles per liter.

10. The reagent of claim 1 wherein the concentration of EDTA is 0.0006 moles per liter.

11. The reagent of claim 1 wherein the concentration of IPA is 0.0325 moles per liter.

12. The reagent of claim 1 wherein the concentration of HOOH is 0.0022 moles per liter.

13. A process for manufacturing one liter of a colorless TMB reagent for detecting HRP, comprising steps of:

(a) mixing TMB in DMSO until dissolved;

(b) combining the mixture of step (a) with a HCl solution;

(c) adding a HPBCD solution to the mixture of step (b);

(d) adding a THH solution to the mixture of step (c);

(e) adding a EDTH solution to the mixture of step (d);

(f) adding a NaAc solution to the mixture of step (e) to adjust the pH of the mixture to about 4.9;

(g) adding HOOH to the mixture of step (f);

(h) adding IPA to the mixture of step (g); and (i) adding DI to the mixture of step (h) to adjust the volume of the mixture to one liter, wherein the concentrations of the ingredients of step (a)–(h) are such that the final mole per liter concentrations of the ingredients are in the range of 0.001 to 0.003 moles per liter for TMB, 0.10 to 0.23 moles per liter for DMSO, 0.02 to 0.035 moles per liter for HCl, 0.004 to 0.01 moles per liter for HPBCD, 0.042 to 0.6 moles per liter for THH, 0.07 to 0.16 moles per liter for NaAc, 0.0004 to 0.004 moles per liter for EDTA, 0.25 to 0.060 moles per liter for IPA, and 0.001 to 0.0033 moles per liter for HOOH.

14. The reagent of claim 13 further including the step (j) adding a NP-4 solution to the mixture of step (i) wherein in step (i) the DI added to the mixture of step (h) is less than one liter by the amount of NP-4 added in step (j) so that the total volume of the reagent is one liter, and wherein the final volume ratio of the NP-4 in the reagent is in the range of 0.10 to 0.20% by volume.

15. The process of claim 14 wherein:

the HPBCD, THH and NaAc solution are prepared prior to their addition in the process of claim 13.

16. The process of claim 15 further including the steps of:

adjusting the pH of the mixture of step (d) to about 2.68 with the NaAc solution and stirring the pH adjusted mixture for about 45 minutes and then adjusting the pH to about 3.8 with the NaAc solution and letting the mixture stand for at least 64 hours; and then adjusting the pH of the mixture to about 4.28 with the NaAc solution.

17. The process of claim 16 wherein the final per cent volume of NP-4 is 0.107%.

18. The process of claim 13 wherein:

in step (a) 0.3 grams per liter of TMB is mixed with 10 milliliters of DMSO;

in step (b) the mixture of step (a) is added to a solution of 4.32 milliliters of HCl in DI;

in step (c) 9.0 grams per liter of HPBCD is added to the mixture of step (d);

in step (d) 55.5 grams per liter of THH is added to the mixture of step (c); and in step (e) 0.24 grams per liter of EDPA is added to the solution of step (d);

in step (g) 2.5 milliliters of HOOH is added to the mixture of step (f); and in step (h) 2.5 milliliters of IPA is added to the mixture of step (g).

19. The method of claim 13 wherein:

the HPBCD, THH and NaAc solution are prepared prior to their addition in the process of claim 13.

20. The process of claim 19 further including the steps of:

adjusting the pH of the mixture of step (d) to about 2.68 with the NaAc solution and stirring the pH adjusted mixture for about 45 minutes and then adjusting the pH to about 3.8 with the NaAc solution and letting the mixture stand for at least 64 hours; and then adjusting the pH of the mixture to about 4.28 with the NaAc solution.

21. The process of claim 20 wherein the final concentration of the ingredients mixed in the method in the claim 13 are 0.00125 moles per liter of TMB, 0.128 moles per liter of DMSO, 0.026 moles per liter of HCl, 0.006 moles per liter of HPBCD, 0.414 moles per liter of THH, 0.10 moles per liter of NaAc, 0.0006 per liter of EDTA, 0.0325 moles per liter of IPA, and 0.0022 moles per liter of HOOH.

22. The process of claim 16 wherein in step (j) 1.07 milliliters of NP-4 is added to the mixture of step (i).

* * * * *